United States Patent
Lin

(10) Patent No.: US 6,258,082 B1
(45) Date of Patent: Jul. 10, 2001

(54) REFRACTIVE SURGERY AND PRESBYOPIA CORRECTION USING INFRARED AND ULTRAVIOLET LASERS

(76) Inventor: J. T. Lin, 730 Willow Run La., Winter Springs, FL (US) 32708

( * ) Notice: Subject to any disclaimer, the term of this patent is extended or adjusted under 35 U.S.C. 154(b) by 0 days.

(21) Appl. No.: 09/303,673

(22) Filed: May 3, 1999

(51) Int. Cl.$^7$ .................................................. A61B 18/18
(52) U.S. Cl. .................... 606/5; 606/4; 606/6; 606/10; 606/13; 372/83; 372/37; 607/89
(58) Field of Search ................................ 606/4–6, 10–12, 606/13, 16, 17; 128/898; 351/204, 206–212; 372/24–26; 359/333, 343, 345

(56) References Cited

U.S. PATENT DOCUMENTS

| | | | |
|---|---|---|---|
| 4,592,065 | * | 5/1986 | De Witte ................................ 372/83 |
| 4,755,999 | * | 7/1988 | Macken .................................. 372/37 |
| 5,484,432 | * | 1/1996 | Sand ........................................ 606/5 |
| 5,520,679 | * | 5/1996 | Lin ........................................... 606/5 |
| 5,630,810 | * | 5/1997 | Machat .................................... 606/5 |
| 5,782,822 | * | 7/1998 | Telfair et al. ............................ 606/5 |
| 5,803,923 | * | 9/1998 | Singh-Derewa et al. ................ 606/5 |
| 5,891,131 | * | 4/1999 | Rajan et al. ............................. 606/5 |
| 5,928,129 | * | 7/1999 | Ruiz ........................................ 600/5 |
| 6,010,497 | * | 1/2000 | Tang et al. .............................. 606/5 |
| 6,019,754 | * | 2/2000 | Kawesch ................................. 606/4 |
| 6,090,102 | * | 7/2000 | Telfair et al. .......................... 606/10 |
| 6,099,522 | * | 8/2000 | Knopp et al. .......................... 606/10 |
| 6,161,546 | * | 12/2000 | Yavitz .................................. 128/898 |

* cited by examiner

Primary Examiner—Linda C. M. Dvorak
Assistant Examiner—Ahmed Farah

(57) ABSTRACT

A method and surgical technique for corneal reshaping and for presbyopia correction are provided. The preferred embodiments of the system consists of a scanner, a beam spot controller and coupling fibers and the basic laser having a wavelength of (190–310) nm, (0.5–3.2) microns and (5.6–6.2) microns and a pulse duration of about (10–150) nanoseconds, (10–500) microseconds and true continuous wave. New mid-infrared gas lasers are provided for the corneal reshaping procedures. Presbyopia is treated by a method which uses ablative laser to ablate the sclera tissue and increase the accommodation of the ciliary body. The tissue bleeding is prevented by a dual-beam system having ablative and coagulation lasers. The preferred embodiments include short pulse ablative lasers (pulse duration less than 200 microseconds) with wavelength range of (0.15–3.2) microns and the long pulse (longer than 200 microseconds) coagulative lasers at (0.5–10.6) microns. Compact diode lasers of (980–2100) nm and diode-pumped solid state laser at about 2.9 microns for radial ablation patterns on the sclera ciliary body of a cornea are also disclosed for presbyopia correction using the mechanism of sclera expansion.

15 Claims, 3 Drawing Sheets

REFRACTIVE SURGERY AND PRESBYOPIA CORRECTION USING INFRARED AND ULTRAVIOLET LASERS

BACKGROUND OF THE INVENTION

1. Field of the Invention

The present invention relates to refractive surgical systems using low-power, infrared and ultraviolet lasers in a predetermined scanning patterns in procedures of photorefractive keratectomy (PRK), laser assisted in situ keratomileusis (LASIK) and laser sclera expansion (LASE), a new procedure for presbyopia correction.

2. Prior Art

Refractive surgeries (or corneal reshaping) including a procedure called photorefractive keratectomy (PRK) and a more recent procedure called laser assisted in situ keratomileusis, or laser intrastroma keratomileusis (LASIK) have been performed mainly by lasers in the ultraviolet (UV) wavelength of (193–213) nm. The commercial UV refractive lasers include ArF excimer laser (at 193 nm) and other non-excimer solid-state lasers such as the one patented by the present inventor in U.S. Pat. No. 5,144,630. Laser corneal reshaping has been conducted by two major beam deliver techniques: the broad beam systems based on patents of L'Esperance et. al. In U.S. Pat. Nos. 4,773,441, 5,019,074, 5,108,338 and 5,163,934; and the scanning small-beam systems based on patent of the present inventor, U.S. Pat. Nos. 5,520,679 and 5,144,630.

Precise, stable corneal reshaping require lasers with strong tissue absorption (or minimum penetration depth) such that thermal damage zone is minimum (less than few microns). Furthermore accuracy of the procedure of vision correction depends on the amount of tissue removed in each laser pulse, in the order of about 0.5 microns. Therefore lasers at UV wavelength (193–213 nm) and at the mid-infrared (2.8–3.2) microns are two attractive ranges which match the absorption peak of protein and water, respectively. UV lasers however have some concerns regarding to the long-term mutagenic effects of the corneal tissue which is less concern in infrared (IR) lasers, noting that the DNA absorption peaks at a UV wavelength about 260 nm. Moreover, UV laser systems suffer problems such as optical damage of the coated mirrors, unstable and short lifetime of the lasing gases and high cost toxic gas of fluorine (for excimer laser). Low beam delivery efficiency and complexity of beam uniformity are other drawbacks of UV refractive lasers.

Refractive surgery using a scanning device and lasers in the mid-infrared (mid-IR) wavelength was first proposed by the present inventor in U.S. Pat. Nos. 5,144,630 and 5,520,679 and later proposed by Telfair et. al., in U.S. Pat. No. 5,782,822, where the generation of mid-IR wavelength of (2.5–3.2) microns were disclosed by various methods including: the Er:YAG laser (at 2.94 microns), the Raman-shifted solid state lasers (at 2.7–3.2 microns) and the optical parametric oscillation (OPO) lasers (at 2.7–3.2 microns). These mid-IR wavelength lasers are proposed as candidates for corneal reshaping due to their strong water absorption.

The present inventor had spent more than five years without success in an attempt to develop mid-IR laser systems based on the above-described prior arts. At the present time, there is no any commercial or clinically practical mid-IR refractive laser system been developed based upon the prior arts because of the inherent problems and difficulties to be discussed as follows.

Er:YAG lasers at long-pulse (or the fundamental mode without Q-switched) were proposed and described for refractive surgery by Seller and Wollensak in "Fundamental mode photoablation of the cornea for myopic correction", Laser and Light in Ophthalmology, pp. 199–203 (1993), and Cozen et al, in PCT Application No. 93/14817. No clinically acceptable results were obtained based on these prior arts because of the following drawbacks: (a) the basic Er:YAG laser having a pulse duration of about 200 microseconds, which was too long to minimize the thermal damage down to that of the UV laser range of few microns, thermal damage zone of about 20–100 microns were reported in long-pulse Er:YAG; b) only low laser repetition rate of about (5–10) Hz are available which limits the procedure speed and to a non-scanning mode; (c) uniform, flat-top beam profiles are not available and only the fundamental Gaussian-type profiles were used in vision corrections limited to myopia only;, other uses of hyperopic and astigmatism corrections can not be performed by the fixed Gaussian beam profile; (d) a 90% Gaussian or better beam profiles without any hot spot are critically required to achieve the expected corrections whose profiles are not predictable, (e) system was operated by a broad beam mode of spot (5–6 mm diameter) which required high laser energy of at least 20 mJ on the corneal surface.

Q-switched Er:YAG lasers at short pulse duration as proposed by Lin and Telfair et al., has not been developed with laser parameters meeting the clinically desired criteria of short pulse width (less than 80 nanoseconds for minimum thermal damage), high repetition rate (at least 40 Hz for reasonable surgery speed) and reliable system components. Development of Q-switched Er:YAG system was inherently limited by factors of optical damage of the Q-switching components, coating problems due to strong water absorption, and the low repetition rate Oess than 25 Hz) due to the cooling problems of the laser rod. To overcome all these inherent drawbacks in an Er:YAG system will not be cost effective and a high maintenance efforts will be required when it is used for refractive surgery. The prior art of Telfari et al proposed a short pulse, less than 50 nanoseconds, Er:YAG system has never been achieved so far in any commercially available system. The reported Er:YAG pulse duration was limited to about 200 nanoseconds.

Another alternative proposed by Lin and Telfail et al., the OPO-laser also had technical difficulties in making a clinically practical system. At this time only low repetition rate OPO-laser (lower than 30 Hz) at low energy (less than 5 mi per pulse) was tested due to the problems of: low conversion efficiency from near-IR to mid-IR wavelength, crystal and optics coating damage at high power and unstable output IR energy due to cooling problems. Therefore a practical OPO-laser system for refractive surgery will be either difficult to make or high cost at high maintenance efforts.

In addition to the above-described OPO-laser, the present inventor also had attempt at no success to develop a Raman-shifted laser due to difficulties of: unstable IR output due to Raman gas flow, optical damage of the coated windows and the inherent back scattering of the Raman signals. Again, a Raman-laser for refractive surgery will be of high cost and difficult to maintain. In addition the system can not be compact in size due to the one-meter long Raman cell.

Corneal reshaping may also be performed by laser thermal coagulation currently conducted by a Ho:YAG laser (at about 2 microns in wavelength) which however, was limited to low-diopter hyperopic corrections. A new procedure for presbyopic correction has recently proposed by implant or diamond knife incision by Schaker in U.S. Pat. Nos. 5,529,076 and 5,722,952. These prior arts, however, have drawbacks of being complexity and time consuming surgery and having risk of side effects. Using lasers for presbyopic corrections or improvements have not been previously proposed.

The above described prior arts which are not clinically practical for refractive uses because of the inherent technical problems or being not cost-effective. In light of this, it is an object of the present invention to provide new laser sources for refractive surgeries and offer the advantages of: compact, low-cost, easy to maintain, operated at mid-IR wavelengths and matching most or all of the clinically desired laser parameters (short pulse, high repetition rate and high water/tissue absorption). These new lasers proposed in this invention will match the two major water absorption peaks at about (2.7–32.) microns and (5.6–6.2) microns.

It is yet another object of the present invention to provide refractive laser systems which offer smooth ablated corneal surface by appropriate beam overlapping and scanning patterns. To further reduce the thermal effects and even corneal hydration, specially designed scanning patterns will be proposed in this invention. Furthermore the exact IR laser beam profiles are not critical in a scanning mode which provides smoother corneal surface by the randomized averaging procedure than the non-scanning lasers which require a 90% Gaussian or better profile without hot spot.

It is yet another object of the present invention to provide refractive laser systems which offer variable beam spot size of about (0.1–2.5) mm for flexible and accurate correction profiles. In the proposed designs, one single system at variable laser beam spots will provide multiple-application including PRK, LASIK and laser sclera expansion (LASE) as introduced earlier. Variable spot size (VSS) controller using electronic shutter or motorized pin-hole will be used in the presently proposed novel devices. It should be noted that the new procedure of LASE has not been reported so far in any UV or IR laser systems because it requires a scanning flexibility of the beam direction, position and the controlled beam spot size and energy for accurate ablation depth on the sclera tissue. We note that the LASE procedure is a method for the treatment of presbyopic patient by corneal sclera expansion caused by removal of a portion of the sclera tissue. After the LASE treatment the patient's accommodation will increase to see both near and far. One of the critical issues of LASE is the corneal bleeding during the laser "cutting". Therefore it is yet another objective of this invention is to combine a coagulation laser with the ablation laser to prevent or minimize the bleeding in the LASE procedure.

According to the discussion in Jacques, S. L., Laser-tissue Interactions; Photochemical, Photothermal and Photomechanical, Lasers in General Surgery, 72t3), 531–558 (1992), we note that photoablation is associated with the UV excimer laser corneal ablation, whereas photomechanical ablation is responsible for the mid-IR laser interaction with the corneal tissue. In the present invention, however, we shall just use the name of "ablation" for the process of photomechanical ablation in describing the mid-IR radiation interaction with the corneal, where corneal tissue fragments was by the mid-IR lasers by its strong absorption in water. We further note that a laser pulse duration of less than 50 nanoseconds for corneal thermal damage claimed by the prior art of Telfair et al may be true for the PRK or LASIK procedures, in which few microns of tissue are removed in each mid-IR pulse. However, an Er:YAG laser Q-switched to a short pulse of 50 nanoseconds has not The condition of short pulse less than 50 nanoseconds not required in the present invention for PRK or LASIK procedures. We propose in this invention that new mid-IR lasers with pulse duration of about (10–100) nanoseconds instead. We also propose that when a laser beam is tightly focused, for example less than 0.15 mm, a long pulse laser may still ablate corneal tissue efficiently at a minimum thermal damage. For the proposed LASE procedure, a much longer laser pulse (in about 10 microseconds or longer) may be used for efficient sclera tissue ablation, as far as the beam spot is less than 150 microns on the corneal surface.

It is yet another object of this invention is to provide novel devices with variable beam spot sizes and multi-stage scanning such that the refractive surgical procedures can be performed within (10–30) seconds without losing the profile accuracy.

It is yet another object of the present invention to provide refractive laser systems which offer a "gas blower" on the corneal surface during the surgery to maintain a controlled level of corneal hydration, which is rather sensitive and critical to the laser ablation rate which is mainly caused by the water absorption in the tissue. The hydration condition of the corneal surface is much more important in IR lasers than in U-V lasers for the process of corneal reshaping.

SUMMARY OF THE INVENTION

The preferred embodiments of the basic refractive surgical lasers to perform the PRK or LASIK procedures include mid-IR lasers of: (a) neutral gas lasers which are governed by transverse electrical (TE) pulse discharged, in the mixtures of xenon, krypton, nitrogen or helium gases and generate wavelengths of about (2.7–3.2) microns; (b) pulsed carbon-dioxide laser (in isotopes of carbon) which is transverse electrical atmosphere (TEA) discharged and frequency doubled into a wavelength of about (5.6–6.2) microns. According to one aspect of the present invention, The preferable scanning mid-IR laser energy per pulse on corneal surface is about (2.0–5.0) mJ for a short pulse of about (10–50) nanoseconds, and about (5–15) mJ for a long pulse of about (50–150) nanoseconds. Focused spot size of about (0.5–2.5) mm will be needed in a scanning system and pulse duration of about (10–150) nanoseconds are also desired for minimum thermal effects.

The other preferred laser parameter of this invention is the laser repetition rate of about (40–500) Hz which will provide reasonable surgical speed and minimum thermal effects. We note that the above preferred two embodiments of the mid-IR spectra, (2.7–3.2) microns and (5.6–6.2) microns are based on the facts that they are the two major water absorption peaks and will result in very efficient corneal tissue removal with minimum thermal damage and precise ablation. We also note that the 6.1 microns spectrum matches the absorption peak of corneal protein. Unlike the UV excimer ArF laser, these mid-IR lasers can be easily delivered through a sapphire fiber at minimum loss.

In another aspect of the present invention is the use of novel devices for beam-spot-size control, where variable spot size (VSS) are required for fast, efficient tissue removal in PRK, LASIK and LASE. The VSS can be achieved by either a shutter at a fixed pin-hole size or a motorized electronic shutter for adjustable beam spot. Our objective in the present invention is to use these VSS devices to achieve: (a) large beam spot of about (1.5–2.5) mm for large area ablation at fast speed (shorter than 20 seconds), and (b) small spot of about (0.1–0.5) mm for small area ablation such as that of LASE correction without losing the accuracy.

Another preferred embodiment of the present invention is to control tho laser output spot size from the laser cavity by an internal magnetic coupler which is used to select a pin-hole size inside the cavity.

To keep the procedure speed, one can use a large spot beam of about 2.0 mm which, however, will lose the accuracy for the ablation of small zone area less than about 3.0 mm range. Therefore VSS device operated in multi-stage procedure is proposed in the present invention. For example, a large beam with (1.5–2.5) mm spot will ablation the first-stage involving an corneal ablation zone size of about (3.5–9.0) mm and followed by the second-stage ablation using a small beam of about (0.3–0.6) mm for the remaining zone of about 3.4 nun.

We should also notice that the problems of central islands, caused by uneven hydration level and shock-wave on the corneal surface, would be mostly reduced by above-introduced VSS designs and controlling these beams scanning in a counter-directions. Moreover, it is another preferred aspect of the present invention to use a random predetermined scanning pattern such that the thermal effect, shock wave and uneven hydration level on the corneal surface can be minimized. The random scanning can be easily achieved by a software design based on the desired correction profiles which is governed by myopic diopter, ablation zone diameter and the position (coordinate) of each scanning beam on the corneal surface. The pre-calculated positions of each scanning spot can be stored and easily assigned to each scanning spot in a randomized means. Details of the equation describing the refractive corrections can be found in J. T. Lin, "Critical review of refractive surgical lasers" in Optical Engineering, vol. 34, 668–675 (1995).

It is yet another preferred embodiment of the present invention to provide refractive laser systems which offer a "gas blower", at a controlled hydration gas mixture or pure predetermined gas of helium or nitrogen, on the corneal surface during the surgery. Controlling the corneal hydration is rather critical to the laser ablation. The hydration control is much more important in IR lasers than in LTV lasers. The gas blower may also reduce the thermal effects on the corneal tissue caused by the mid-IR lasers.

For the purpose of smooth ablation corneal surface, a computer-controlled galvanometer-pair coated with high-reflecting at the main mid-IR beam is used in the present invention. Scanning patterns including circular and oriented linear scan are used for beam profile averaging (BPA) to achieve the smooth tissue surface. We had tested hundreds of PMMA ablated sheets to conclude that only rough surfaces can be obtained without this BPA design. Quantitative comparisons are made in our laboratory by the diopter readings of the ablated PMMA sheets in a lensmeter. The scanning laser offers a clearly readable diopters (up to about 5.0) on the ablated PMMA sheets whereas those from the conventional non-scanning lasers are not readable at all due to the high surface light scattering.

We should note that the idea refractive surgical laser should perform and achieve: fast procedure to reduce the eye-motion-effects, accurate ablation profile (particularly in the presbyopia small zone application), good clinical results (smooth ablated cornea surface, reduced haze and regression), low system cost and easy maintenance. The proposed novel devices of VSS and the multi-stage ablation patterns described in the present invention provide us a unique means to achieve these objectives.

It would be very difficult for any non-scanning lasers to perform the new application of laser sclera expansion (LASE) for presbyopia correction which requires small beam spot, low-energy and flexible scanning patent to ablate the sclera tissue. The preferred embodiments of the basic ablative lasers to perform the LASE procedures by removing portion of the sclera tissue include lasers of: (a) diode laser at about 980 nm, 1.5 microns, and 1.9 microns, (b) diode-laser pumped Er:YAG laser at about 2.94 microns, (c) the mid-IR gas lasers of about (2.7–3.2) microns and (5.6–6.2) microns and (d) short wavelength ultraviolet lasers of about (190–310) nm including ArF(193 nm) and XeCl (at 308 nm) excimer lasers and (e) solid-state OPO-lasers of about (2.7–3.2) microns. We propose that when a laser beam is tightly focused, for example less than 0.15 mm, a long pulse laser can still ablate corneal sclera tissue efficiently with minimum thermal damage. Thermal damage zone size of about (5–20) microns is clinically acceptable for the sclera ablation which has a typical ablation depth of about (400–700) microns. Therefore laser pulse duration for diode lasers at quasi-continuous-wave (QCW) mode or diode-pumped free-running Er:YAG laser with a typical pulse duration of about (10–500) microseconds are proposed in the invention.

The preferred embodiments of the basic coagulation lasers to prevent or minimize the corneal bleeding during the LASE procedures include the following lasers at long pulse duration: (a) visible lasers with wavelength of (500–690) nm, (b) infrared lasers at wavelength of about 1.0, 1.5, 2.0 and 2.9 microns, in which the corneal tissue absorption of these radiation will cause the thermal effects for coagulation to occur.

The ophthalmic applications of the IR laser systems described in the present invention should include, but not limited to, photorefractive keratectomy (PRK), phototherapeutic keratectomy (PTK), intrastroma photokeratectomy, laser assisted in situ keratomileusis (LASIK) for myopic, hyperopic, astigmatism and laser sclera expansion (LASE) for presbyopia corrections.

DETAILED DESCRIPTION OF THE PREFERRED EMBODIMENT

We should first briefly present some of the theoretical background of the present invention regarding to the ablation efficiency or the procedure speed, and the ablation threshold, fluency and intensity, two of the main objectives of the present invention. Greater detail regarding to the theoretical aspects can be found in a paper published by the present inventor in: "Critical Review of Refractive Surgical Lasers", Optical Engineering, Vol. 34, pp.668–675, (1995).

Given a laser energy per pulse of E (in mJ), a fluency of F (in $mJ/cm^2$) may be achieved by focusing the beam into an area of A and F=E/A. For corneal tissue ablation, either photoablation or photomechanical ablation (defined by reference of Jacques, S. L., "Laser-tissue Interactions; Photochemical, Photothermal and Photomechanical," Lasers in General Surgery, 72(3), 531–558,1992). For an ablation to occur, the laser intensity I (in MW/cm$^2$) must be higher than the an ablation threshold (AT) of about (10–20) MW/cm$^2$ for UV-laser, and about (50–100)MW/cm$^2$ for IR lasers where I-F/t, t being the pulse duration. Therefore it is always possible to tightly focus a pulsed-laser beam and achieve the AT value even for a low-energy laser of (0.1–1.0) mJ for UV lasers and (0.5–5) mJ for mid-IR lasers.

Taking a typical mid-IR laser of 15 nanosecond pulse width as an example, small spot size of about 1.0 mm is needed on the corneal surface when the available mid-IR energy is limited to about 3 mJ range, whereas about 9 mJ will be needed when spot size of 2 mm is used.

In addition to the above described ablation threshold (governed by laser intensity and pulse width), the procedure speed (governed by laser averaged power) is another important concept needed to be addressed. The drawback of using a low-energy, small-spot laser for refractive procedures is that the operation time will be longer than that of a large-spot but high-power laser. However, the operation time may be shortened by using a high repetition-rate laser. It is important to note that given an averaged power P, the laser intensity must be above the ablation threshold (AT) by either beam focusing or increasing the laser energy or keeping the laser pulse short enough.

The preferred embodiments disclosed in the present invention will be based upon the above described theory. Beam focusing and scanning are always required to achieve the ablation threshold and ablation smoothness for the proposed low-energy lasers. The individual beam profile in the scanning system is not as critical as that of prior non-scanning systems which require a uniform overall profile.

Figure 1:
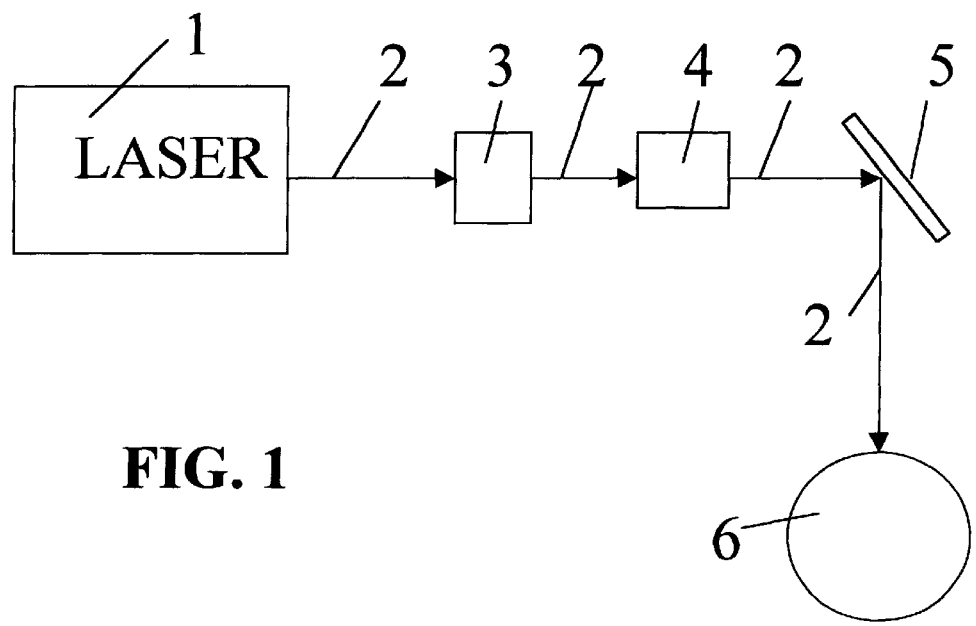
FIG. 1 is a block diagram of a refractive laser system consisting of an mid-IR laser couple to a beam spot controller, scanning device, and reflector for refractive surgery.

Referring to FIG. 1, a refractive laser system in accordance with the present invention comprises a basic laser 1 having wavelength 2 was focused by a beam spot controller 4 into the scanning device 4 and reflected by a coated (high-reflecting at the wavelength 2 of IR beam) mirror 5 into the target, patient's cornea surface 6.

Still referring to FIG. 1, the basic laser 1, according to the present invention, the preferred embodiments of the basic refractive surgical lasers to perform the PRK or LASIK procedures include mid-IR lasers of: (a) neutral gas lasers which are governed by transverse electrical (TE) pulse discharged, in the mixtures of xenon, krypton, nitrogen or helium gases and generate wavelengths of about (2.7–3.2) microns; Co) pulsed carbon-dioxide laser (in isotopes of carbon) which is transverse electrical atmosphere (TEA) discharged and frequency doubled into a wavelength of about (5.6–6.2) microns. According to one aspect of the present invention, the preferable scanning mid-IR laser energy per pulse on corneal surface is about (2.0–5.0) mJ for a short pulse of about (10–50) nanoseconds, and about (5–15) mJ for a long pulse of about (50–150) nanoseconds. Focused spot size of about (0.5–2.5) mm will be needed in a scanning system and pulse duration of about 150 nanoseconds or shorter are also desired for minimum thermal effects. The other preferred laser parameter of this invention is the laser repetition rate of about (40–500) Hz which will provide reasonable surgical speed and minimum thermal effects.

Figure 2:
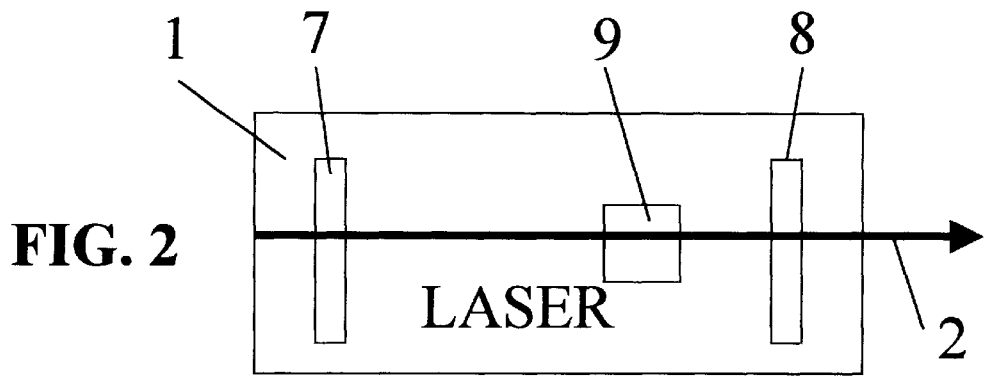
FIG. 2 presents the schematics of the internal magnetic coupler for the selection of output beam spot size.

Referring to FIG. 2, the basic mid-IR gas laser cavity 1 has a pair of reflecting windows 7 and 8 to generate the output beam of 2 which has a beam spot size of about (2–10) mm diameter controlled by the internal magnetic coupler, or pin-hole 9. This magnetic coupler when is at the "on" position will limited the internal beam propagation to a small area and generate a circular output beam which can be easily focused into a small spot on the corneal surface about (0.05–0.5) mm. On the other hand when the magnetic coupler is at the "off" position, a larger output beam, with higher energy, can be generated for situation that a larger beam, size of about (0.5–2.5) mm is desired for a faster procedures in PRK or LASIK. We note that the small beam spot of less than 0.15 mm is normally needed in the new procedure of LASE to be discussed later.

Figure 3:
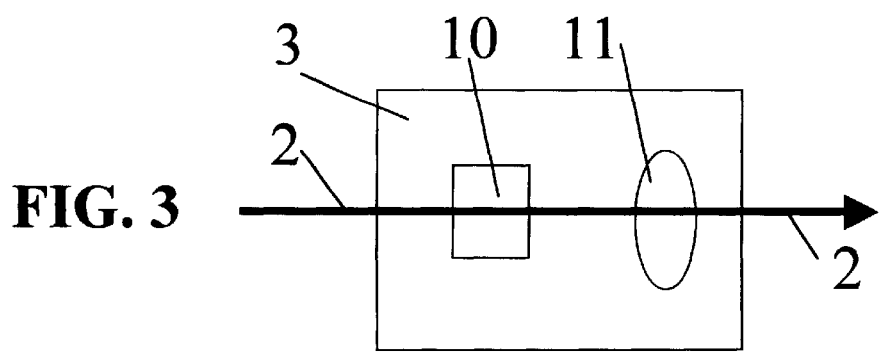
FIG. 3 presents the schematics of the external pin-hole spot size controller.

As shown in FIG. 3, the beam spot external controller 3 consisting of a motorized electronic shutter 10 and a focusing lens 11, where the pin-hole size of the electronic shutter (made by, for example, Melles Griod) are continuously adjustable in the range of about (1.5–10) mm to reduce the output beam from the laser cavity 2 to a spot size of about (0.05–2.5) mm on the corneal surface.

Figure 4:
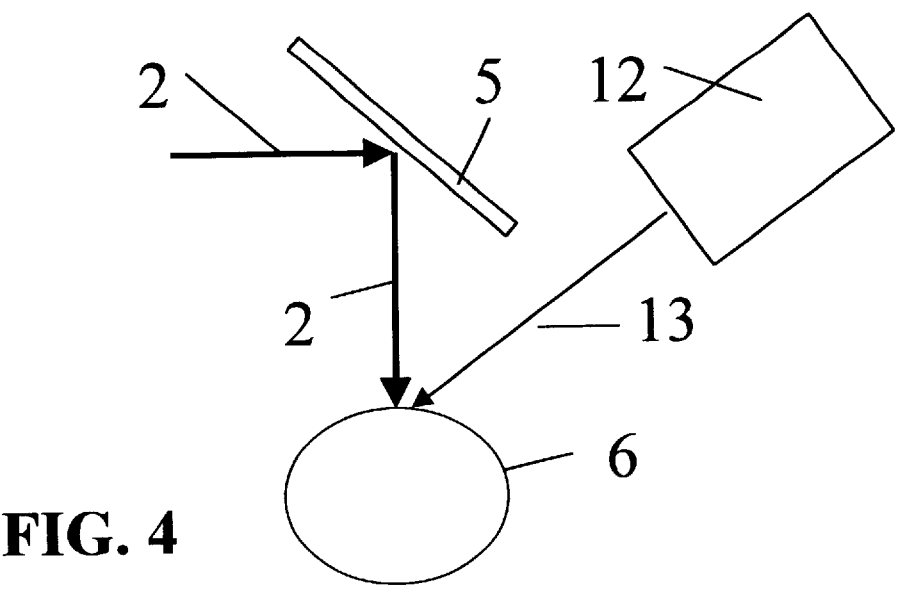
FIG. 4 shows schematics for a gas blower to control the hydration level of the corneal surface during the laser ablation.

Referring to FIG. 4, the output beam from the laser cavity 2 is reflected by a mirror 5 onto the corneal surface 6 in which the hydration level is controlled by a gas blower 12. The preferred embodiments of this invention is to use gases 13 which include nitrogen or helium and apply to the target area of the cornea. These gases 13 will have a controlled speed and hydration level. Furthermore, another preferred embodiment of this invention is to use cool gases 13 to minimize the thermal effects on the corneal surface caused by the mid-IR lasers.

Figure 5:
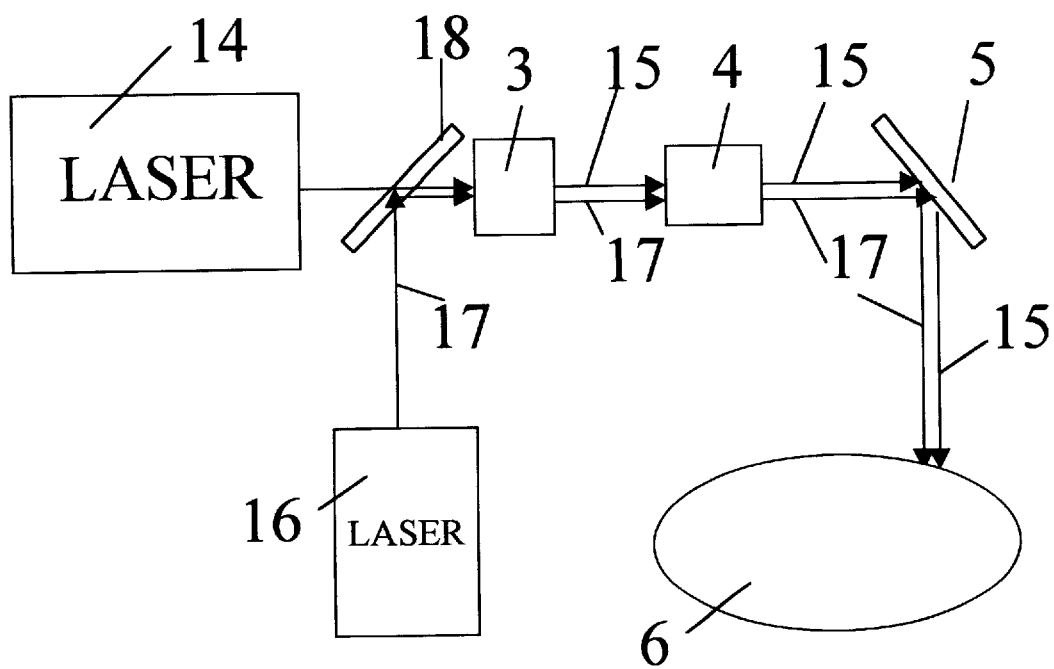
FIG. 5 illustrates the dual beam device for presbyopia correction.

FIG. 5 shows the schematics of a system for presbyopia correction by laser sclera expansion (LASE). The selected basic ablative laser 14 having wavelength 15 is coupled to a coagulation laser 16 having wavelength of 17 by a beam splitter 18 and focused by a spot controller 3 into a scanner device 4. These two beams 15 and 17 are then reflected by a dual-band coated high-reflecting mirror 5 onto the limbo area of the cornea 6.

In FIG. 5, the preferred embodiments of the basic ablative lasers 14 to perform the LASE procedures include lasers of: (a) diode laser at about 980 nm, 1.5 microns, and 1.9 microns, (b) diode-laser pumped Er:YAG laser at about 2.94 microns, (c) the mid-IR gas lasers of about (2.7–3.2) microns and (5.6–6.2) microns and (d) short wavelength ultraviolet lasers of about (190–310) nm including ArF(193 mn) and XeCl (at 308 nm) excimer lasers and (e) solid-state OPO-lasers of about (2.7–3.2) microns. We propose that when a laser beam is tightly focused, for example less than 0.15 mm, a long pulse laser can still ablate corneal sclera tissue efficiently with minimum thermal damage. Thermal damage zone size of about (5–20) microns is clinically acceptable for the sclera ablation which has a typical ablation depth of about (500–600) microns. Therefore laser pulse duration for diode lasers at quasi-continuous-wave (QCW) mode or diode-pumped free-running Er:YAG laser with a typical pulse duration of about (10–500) microseconds are proposed in the invention.

Still referring to FIG. 5, the proposed LASE procedure with efficient sclera tissue ablation, the preferred embodiments of the invention for the pulse duration of the ablative laser 16 are: (a) about (10–200) microseconds for quasi-continuous-wave (QCW) diode lasers at wavelength of about 980 nm, 1.5 microns, and 1.9 microns, (b) about (50–500) microseconds for diode-pumped Er:YAG laser, (c) about (10–200) nanoseconds for pulsed mid-IR gas or solid-state lasers at about (2.7–3.2) microns and (5.6–6.2)

microns and (d) short pulse laser of about (1–100) nanoseconds for the ultraviolet lasers with wavelength of about (190–310) nm. For minimum thermal damage and minimum scars on the corneal surface after the LASE procedure, the preferred embodiments of this invention include a laser beam spot size of about (5–500) microns on the ablated sclera tissue. Depending on the pulse duration, beam spot size and wavelength, the laser energy per pulse needed for sclera ablation will be about (0.5–15) mJ on the corneal surface.

The preferred embodiments in FIG. 5 for the basic coagulation laser 16 to prevent or minimize the corneal bleeding during the LASE procedures include the following lasers at long pulse duration or continuous wave (CW): (a) visible lasers with wavelength of (500–690) nm, (b) infrared lasers at wavelength of about 0.98, 1.5, 2.0 and 2.9 microns, in which the corneal tissue absorption of these radiation will cause coagulation to occur. The preferred embodiments of the invention for the selected coagulation lasers include pulse duration of at least 100 microseconds and averaged power on the corneal surface of about (0.1–5.0) W, for spot size of about (0.1–1.0) mm. We note that the coagulation features of a laser are mainly governed by the long pulse duration and large spot size (or lower fluency) on the corneal surface. For a given wavelength longer than about 980 nm, a laser may be an ablative one or a coagulation one. When a laser is tightly focused, less than about 100 microns, the high fluency or peak power may start to perform ablative than coagulation in its interaction to tissues. For ultraviolet lasers shorter than 310 nm, however, coagulation effects will be minimum even at a large beam size.

Figure 6:
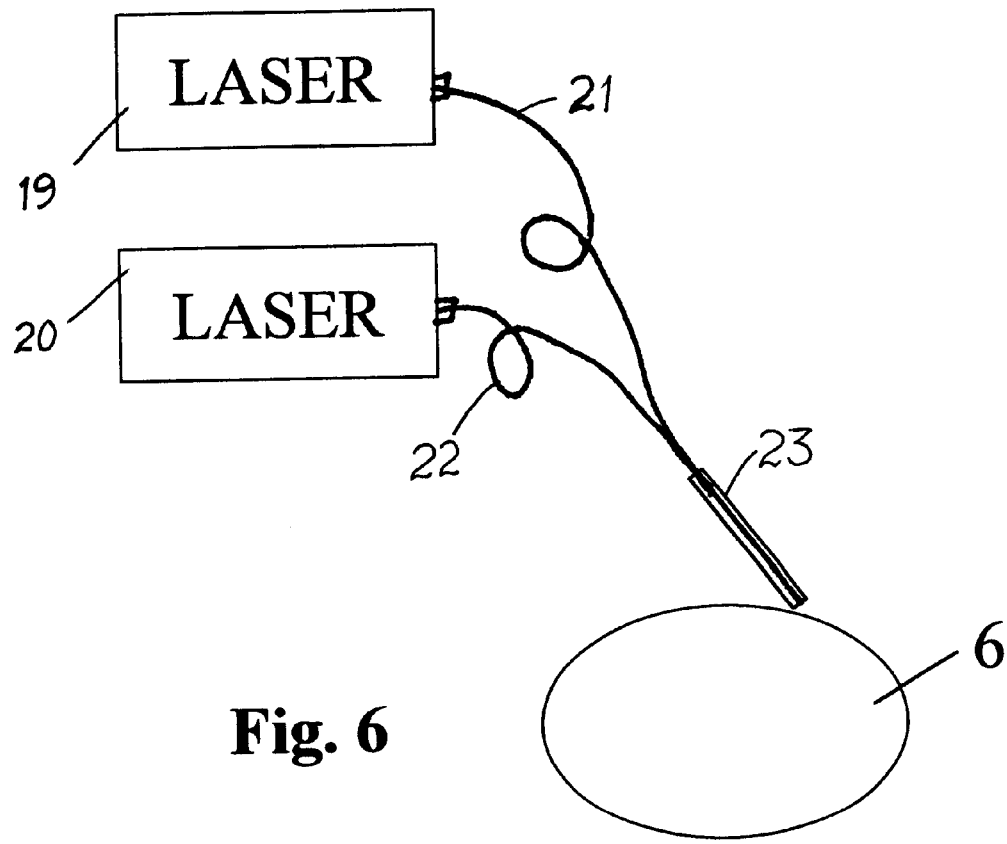
FIG. 6 shows the schematics of fiber-coupled diode lasers or diode-pumped laser for presbyopic correction system.

FIG. 6 shows the LASE procedures performed by selected diode lasers or diode-pumped laser which are fiber-coupled on to the corneal surface. The basic ablative laser 19 is coupled to a fiber 21 and combined by another fiber jacket 23 with the coagulation laser 20 after it is coupled to a fiber 22, where fibers 21 and 22 are highly transparent (better than 85% in about one meter long) to the wavelength of laser 19 and 20, respectively. The combined output two wavelengths laser is then used to ablation and coagulate the sclera tissue to achieve ablation patterns to be described in FIG. 7.

Figure 7:
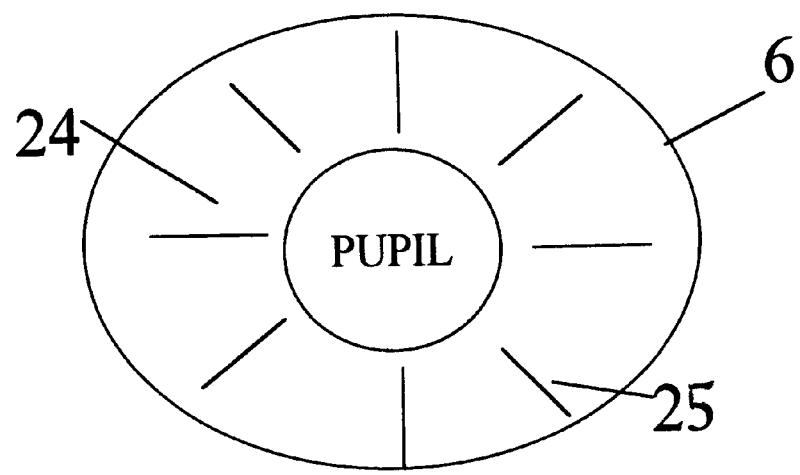
FIG. 7 shows the presbyopia correction patterns on the sclera area.

FIG. 7 shows the LASE patterns, where the selected lasers are focused onto the cornea surface around the limbus area 24. Radial ablation patterns are performed in the anatomic limbus area of the sclera ciliary body. The ablation depth of the sclera ciliary tissue is about (400–700) microns with each of the radial length 25 of about (2.5–3.5) mm adjustable according to the optimal clinical outcomes including minimum regression and maximum accommodation for the presbyopic patients. The preferred radial ablation shall start at a distance about (4.0–5.5) mm from the corneal center out to the limbus area.

Referring to FIG. 7, the preferred embodiments to generate the radial patterns on the sclera area include: (a) using the computer controlled scanning mirrors which move in x and y directions; (b) using a mechanical translator which is attached to the fiber end of the coupled ablative and coagulation lasers and cause the lasers to move along the predetermined patterns, and (c) manually move the fiber-coupled lasers along a line to generate the linear patterns. For precise and controllable ablation depth of the sclera tissue, methods (a) and (b) are preferred.

We also propose that overlapping of the scanning or translating beam is preferred for smooth, uniform and controlled depth of the ablated sclera. Calibration on materials including PMMA plastic sheet is preferred in order to clinically pretest the ablation depth of the sclera tissue. Measurement the depth of the ablated sclera tissue can be conducted by preset diamond knife instrument or ultrasound.

In this invention, we define the refractive surgeries by performing either PRK for corneal surface ablation or LASIK for intrastroma ablation and in general we name these procedures as corneal reshaping. The presbyopia correction, however, is referred as the removal of the sclera tissue.

While the invention has been shown and described with reference to the preferred embodiments thereof, it will be understood by those skilled in the art that the foregoing and other changes and variations in form and detail may be made therein without departing from the spirit, scope and teaching to the invention. Accordingly, threshold and apparatus, the ophthalmic applications herein disclosed are to be considered merely as illustrative and the invention is to be limited only as set forth in the claims.

I claim:

1. A method of performing refractive surgery by reshaping a portion of corneal tissue, said method comprising the steps of:

selecting a gas laser generated by transverse electrical discharge in a mixture of neural gases including at least helium gas and having a pulsed output beams of predetermined mid-IR wavelength of (2.7–3.2) microns;

selecting a beam spot controller mechanism, said spot controller consisting of an internal magentic coupler integrated inside the laser cavity having a pin-hole size of about (2–10) mm;

focusing the output beam to a spot size of about (0.05–2.5) mm on the corneal surface;

selecting a scanning mechanism for scanning said selected laser output beam;

coupling said laser beam to a scanning device for scanning said laser beam over a predetermined corneal surface area to remove corneal tissue, whereby a patient's vision is corrected by reshaping the cornea.

2. A method of claim 1, in which the hydration level of said corneal surface area is controlled by a gas blower such that a consistent tissue ablation rate can be achieved.

3. A method for improving presbyopic patient's vision by removing a portion of the sclera tissue from an eye of a patient, said method comprising the steps of:

selecting an ablative laser for removing sclera tissue by focusing said ablative laser to a spot size of about (5–800) microns on the corneal surface;

selecting a scanning mechanism for scanning said ablative laser;

coupling said ablative laser to a scanning device for scanning said ablative laser over a predetermined area outside the corneal limbus to remove said sclera tissue, whereby a patient's near vision is improved by the increase of the corneal lens accommodation.

4. A method of claim 3, in which said ablative laser is a gas laser having an output wavelength of about (2.7–3.2) microns, energy per pulse of about (0.5–15) mJ on corneal surface and a pulse duration less than 150 nanoseconds.

5. A method of claim 3, in which said ablative laser is a mid-IR solid-state laser having a wavelength of about (2.7–3.2) microns.

6. The method of claim 3, in which said ablative laser includes pulsed radiation generated by transverse electrical discharge carbon dioxide laser which is frequency-doubled into a laser having a wavelength of about (5.6–6.2) microns, energy per pulse of about (2–15) mJ on the corneal surface.

7. A method of claim 3, in which said ablative laser is a diode laser having a wavelength of about 980 nm.

8. A method of claim 3, in which said ablative laser is a diode laser having a wavelength of about (1.4–2.1) microns.

9. A method of claim 3, in which said ablative laser is a diode-pumped Er:YAG laser having a wavelength about 2.9 microns and a pulse duration less than 500 microseconds.

10. A method of claim 3, in which said ablative laser is an ultraviolet laser having wavelength of about (190–310) nm.

11. A method of claim 3, in which said sclera tissue is coagulated by a laser having a wavelength of about (0.5–3.2) microns, an average power of about (0.1–5.0) W on the corneal surface, spot size of about (0.1–1.0) mm, and a pulse duration longer than about 200 seconds.

12. A method of claim 3, in which said ablative laser is fiber-coupled and combined with a coagulation laser and delivered to the corneal surface.

13. A method of claim 3, in which said sclera tissue is ablated in radial patterns having a length about (2.5–3.5) mm and a depth about (400–700) microns.

14. A method of claim 3, in which said sclera tissue is ablated in radial patterns by a computer-controlled scanning mechanism.

15. A method of claim 3, in which said sclera tissue is ablated in radial patterns by a translation mechanism.

* * * * *